United States Patent [19]

Gilman

[11] Patent Number: 4,832,008
[45] Date of Patent: May 23, 1989

[54] WOUND DRESSING WITH RELEASE SHEETS STRIP

[75] Inventor: Thomas Gilman, Lake Zurich, Ill.

[73] Assignee: The Kendall Company, Boston, Mass.

[21] Appl. No.: 153,871

[22] Filed: Feb. 9, 1988

[51] Int. Cl.4 .................. A61F 13/00; A61F 15/00
[52] U.S. Cl. .................................. 128/155; 128/156; 206/440; 604/304
[58] Field of Search .................. 128/155, 156, 335; 206/440, 441; 604/304, 307

[56] References Cited

U.S. PATENT DOCUMENTS

| | | | |
|---|---|---|---|
| 2,897,961 | 8/1959 | Bush | 206/441 |
| 4,513,739 | 4/1985 | Johns | 128/156 |
| 4,598,004 | 7/1986 | Heinecke | 128/156 |
| 4,600,001 | 7/1986 | Gilman | 604/304 |
| 4,646,731 | 3/1987 | Brower | 128/156 |
| 4,684,557 | 8/1987 | Pennace et al. | 428/452 |
| 4,753,232 | 6/1988 | Ward | 128/156 |

FOREIGN PATENT DOCUMENTS 0842617  7/1960  United Kingdom ................ 128/155

Primary Examiner—Richard J. Apley
Assistant Examiner—Paul Prebilic
Attorney, Agent, or Firm—Powell L. Sprunger

[57] ABSTRACT

A wound dressing comprising, an elastomeric film having adhesive on a front surface thereof, and a pair of opposed end margins. The dressing has a release sheet for releasably covering the adhesive, and a pair of strips releasably secured to the end margins and having adhesive on a front surface of the strips, with the strip adhesive being more aggressive to the release sheet than the film adhesive to the strips, wherein the strips are more aggressively attached to the film adhesive than the release sheet is attached to the film adhesive.

5 Claims, 1 Drawing Sheet

WOUND DRESSING WITH RELEASE SHEETS STRIP

BACKGROUND OF THE INVENTION

The present invention relates to wound dressings.

Certain wound dressings which are now widely used in hospitals and elsewhere consist of thin elastomeric films coated with adhesive. These composites are difficult to deliver to the patient, due to the flimsy nature of the film and the presence of the adhesive.

Several dressings have been disclosed in attempts to make it more easy to deliver such products. U.S. Pat. No. 4,513,739 describes a system where an adhesive coated film dressing has a means attached to the edges of the film to retard the release of the dressing from the protective backing, or release liner, which covers the adhesive. This allows the release liner to be partially removed for bandage application while remaining attached for handling purposes.

Another dressing utilizing this same general approach is described in U.S. Pat. No. 4,598,004. In this disclosure, the dressing is perforated at the margins. The release liner is attached firmly to the perforated margin, and releasably to the remainder of the dressing. In use, the liner is partially removed for application of the dressing, and then the perforated portions are removed by pulling harder on the liner.

SUMMARY OF THE INVENTION

A principal feature of the present invention is the provision of an improved wound dressing.

The wound dressing of the present invention comprises an elastomeric film having adhesive on a front surface thereof, and a pair of opposed end margins. The dressing has release sheet means to releasably cover the adhesive. The dressing has a pair of strips releasably secured to the end margins.

A feature of the present invention is that the strips have adhesive on a front surface of the strips.

Another feature of the invention is that the strip adhesive is more aggressively attached to the release sheet means than the film adhesive to the strips.

A further feature of the invention is that the strips are more aggressively attached to the film adhesive than the release sheet means is attached to the film adhesive.

Thus, a feature of the invention is that release sheet means can be peeled to the strips for placement of the film on a patient while the strips retain the release sheet means to facilitate placement of a central portion of the film.

Yet another feature of the invention is that the end margins can be applied by peeling further to remove the strips (which remain attached to the release sheet means) from the film. The end margins are applied to the patient as the peeling takes place.

Further features will become more fully apparent in the following description of the embodiments of this invention and from the appended claims.

DESCRIPTION OF THE PREFERRED EMBODIMENTS

Figure 1:
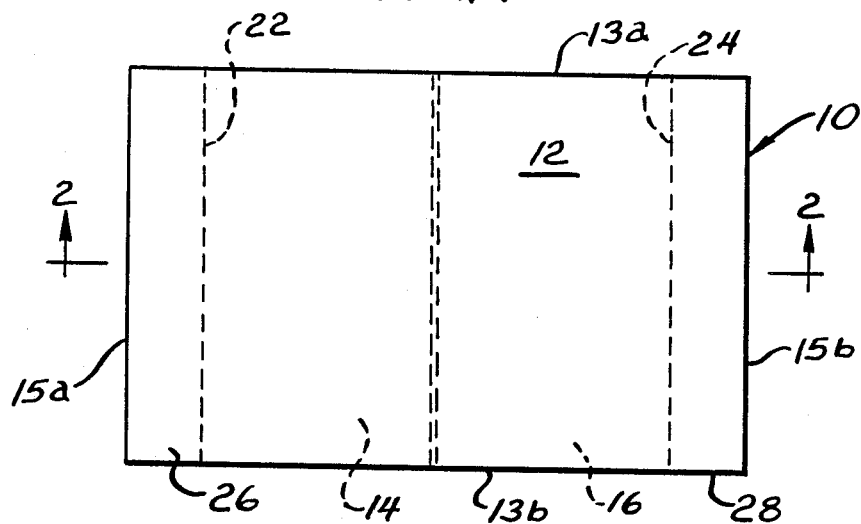
FIG. 1 is a top plan view of a wound dressing of the present invention.
Figure 2:
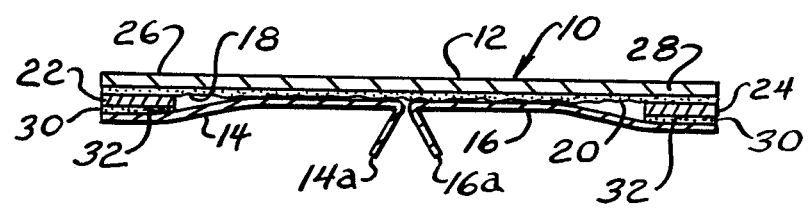
FIG. 2 is a sectional view taken substantially as indicated along the line 2—2 of FIG. 1.

Referring now to FIGS. 1 and 2, there is shown a wound dressing generally designated 10 having an elastomeric film 12 and a pair of release sheets 14 and 16 which extend to a central portion of the film 12 from end portions thereof. The film has a pair of side edges 13a and 13b, and a pair of end edges 15a and 15b connecting the side edges 13a and 13b. The film 10 may be of any suitable type which is water vapor permeable, such as Hytrel, Trademark of E.I. du Pont de nemours having a polyester-polyether block polymer film. This film 10 has a layer of adhesive 18 on a front surface 20 of the film 10. The adhesive may comprise suitable pressure sensitive adhesive. The release sheets 14 and 16 may have a suitable silicone release coating facing the adhesive 18 such that the release sheets 14 and 16 are releasably attached to the adhesive 18, and the release sheets 14 and 16 may have associated tabs 14a and 16a to facilitate their removal.

The dressing 10 has a pair of elongated paper strips 22 and 24 releasably attached to end margins 26 and 28 of the film 12. The strips 22 and 24 have a second adhesive 30 on a front surface 32 thereof, such as a silicone adhesive, which bonds the strips more aggressively to the release sheets 14 and 16 than they are bonded to the adhesive 18.

The strips 22 and 24 should be more aggressively attached to the film 12 than the release sheets to the film 12 to provide additional resistance to peeling in the region of the strips 22 and 24. This is accomplished by coating the strips with a different release coating than is used on the sheets 14 and 16.

In use, the dressing 10 is placed over a wound or the patient, and the tabs 14a and 16a are grasped in order to peel the release sheets 14 and 16 from the adhesive 18 until the release sheets are peeled to the strips 22 and 24. The strips 22 and 24 hold the release sheets in place while the central portion of the film 12 is applied over the wound after which the strips are peeled from the film 10, and the end margins 26 and 28 are applied to the patient as the peeling takes place.

The foregoing detailed description is given for clearness of understanding only, and no unnecessary limitations should be understood therefrom, as modifications will be obvious to those skilled in the art.

I claim:

1. A wound dressing comprising:
   an elastomeric film having adhesive on a front surface thereof, and a pair of opposed end margins;
   release sheet means to releasably cover said adhesive; and
   a pair of strips releasably secured to said end margins and having adhesive on a front surface of the strips, said strip adhesive being more aggressively attached to the release sheet means than the film adhesive is attached to the strips, wherein the strips are more aggressively attached to the film adhesive than the release sheet means is attached to the film adhesive.

2. The dressing of claim 1 wherein said release sheet means comprises a pair of release sheets extending to a central portion of the film.

3. The dressing of claim 1 wherein said strip adhesive comprises a silicone adhesive.

4. The dressing of claim 1 wherein said strips comprise paper.

5. The dressing of claim 1 wherein the film is permeable to water vapor.